United States Patent
Higham et al.

(10) Patent No.: US 7,332,117 B2
(45) Date of Patent: *Feb. 19, 2008

(54) ION TREATED HYDROGEL

(75) Inventors: Paul Higham, Ringwood, NJ (US); Philip F. Williams, III, Teaneck, NJ (US); John Lapszynski, Oak Ridge, NJ (US); Chau Ngo, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 608 days.

This patent is subject to a terminal disclaimer.

(21) Appl. No.: 10/847,077

(22) Filed: May 17, 2004

(65) Prior Publication Data

US 2004/0212130 A1    Oct. 28, 2004

Related U.S. Application Data

(63) Continuation of application No. 10/020,389, filed on Oct. 30, 2001, now Pat. No. 6,783,721.

(51) Int. Cl.
*B29C 71/00*    (2006.01)
(52) U.S. Cl. .................. 264/232; 264/328.1; 264/233; 264/234
(58) Field of Classification Search ............... None
See application file for complete search history.

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 3,957,362 A | 5/1976 | Mancini et al. |
| 3,992,563 A | 11/1976 | Tanaka |
| 4,173,606 A | 11/1979 | Stoy et al. |
| 4,309,777 A | 1/1982 | Patil |
| 4,349,921 A | 9/1982 | Kuntz |
| 4,452,776 A | 6/1984 | Refojo |
| 4,550,001 A | 10/1985 | Suminoe et al. |
| 4,663,358 A | 5/1987 | Hyon et al. |
| 4,714,469 A | 12/1987 | Kenna |
| 4,772,287 A | 9/1988 | Ray et al. |
| 4,904,260 A | 2/1990 | Ray et al. |
| 4,911,718 A | 3/1990 | Lee et al. |

(Continued)

OTHER PUBLICATIONS

Structure and Properties of Poly (vinyl alcohol)-Iodine Complex Formed in the Crystal Phase of Poly (vinyl alcohol) Films, Y. Choi and K. Miyasaka, Journal of Applied Polymer Science, vol. 51, 613-618 (1994).

(Continued)

*Primary Examiner*—Christina Johnson
*Assistant Examiner*—Keith Godfrey
(74) *Attorney, Agent, or Firm*—Lerner, David, Littenberg, Krumholz & Mentlik, LLP

(57) ABSTRACT

A high strength hydrogel having a constant swelling pressure upon implantation and thereafter is formed by preparing a hydrogel solution and then injecting the solution into a mold and cause to gel. The molded gel is then washed in a saline solution from about one day to twelve weeks, after which the gel is irradiated for sterilization purposes, dehydrated and packaged. The pre-treatment with the use of a physiologic solution results in an implant which exhibits a constant swelling pressure profile after implantation.

30 Claims, 3 Drawing Sheets

U.S. PATENT DOCUMENTS

| | | |
|---|---|---|
| 4,988,761 A | 1/1991 | Ikada et al. |
| 5,047,055 A | 9/1991 | Bao et al. |
| 5,149,052 A | 9/1992 | Stoy et al. |
| 5,192,326 A | 3/1993 | Bao et al. |
| 5,534,028 A | 7/1996 | Bao et al. |
| 5,674,283 A | 10/1997 | Stoy |
| 5,681,871 A | 10/1997 | Molock et al. |
| 5,705,780 A | 1/1998 | Bao |
| 5,733,563 A | 3/1998 | Fortier |
| 5,976,186 A | 11/1999 | Bao et al. |
| 5,981,826 A | 11/1999 | Ku et al. |
| 6,060,534 A | 5/2000 | Ronan et al. |
| 6,165,201 A | 12/2000 | Sawhney et al. |
| 6,187,048 B1 | 2/2001 | Milner et al. |
| 6,232,406 B1 | 5/2001 | Stoy |
| 6,264,695 B1 | 7/2001 | Stoy |
| 6,368,522 B1 | 4/2002 | Ansell et al. |
| 6,383,609 B1 | 5/2002 | Annergren et al. |
| 2001/0051134 A1* | 12/2001 | Pandya ............ 424/44 |

OTHER PUBLICATIONS

Hydrogels and Biodegradable Polymersfor Bioapplications, American Chemical Society, 1994.

Swelling Pressure of Poly(Glyceryl Methacrylate) Hydrogels, M. Refojo, pp. 697-704; 1972.

\* cited by examiner

ION TREATED HYDROGEL

The present application is a continuation of U.S. patent application Ser. No. 10/020,389 filed Oct. 30, 2001 now U.S. Pat. No. 6,783,721.

BACKGROUND OF THE INVENTION

This invention relates to a prosthetic intervertebral disc nucleus. More particularly it relates to an artificial disc nucleus made of a hydrogel material that exhibits a stable swelling pressure characteristic after implantation, i.e., the water content of the material and the size of the implant made from the material remains stable in vivo and also the time required to bring the material to a stable state prior to implantation can be reduced.

The intervertebral disc is a complex joint anatomically and functionally. It is composed of three component structures: the nucleus pulposus (the nucleus), the annulus fibrosus (the annulus) and the vertebral end-plates. The biochemical composition and anatomical arrangements within these component structures are related to the biomechanical function of the disc.

The nucleus occupies about 25-40% of the total disc cross-sectional area. It is primarily composed of mucoid material containing mainly proteoglycans with a small amount of collagen. The proteoglycans consist of a protein core with chains of negatively charged keratin sulphate and chondroitin sulphate covalently attached thereto. Due to these constituents, the nucleus is a loose hydrogel which usually contains about 70-90% water by weight. Although the nucleus plays an important role in the biomechanical function of the disc, the mechanical properties of the disc are not well known, largely because of the loose hydrogel nature of the nucleus.

As the nucleus is surrounded by the annulus and vertebral end-plates, and the negatively charged sulphate groups are immobilized due to the attachment of these groups to the polymer matrix, the matrix has a higher concentration of counter ions than its surroundings. This ion concentration results in a higher osmotic pressure than the annulus e.g., ranging from about 0.1 to about 0.3 MPa. As a result of the high fixed charge density of the proteoglycan the matrix exerts an osmotic swelling pressure that can support an applied load in much the same way as air pressure in a tire supports the weight of a car.

It is the osmotic swelling pressure and hydrophilicity of the nucleus matrix that offers the nucleus the capability of imbibing fluid until it is balanced with the internal resistance stresses, resulting from the tensile forces of the collagen network, and the external stresses due to the loads that are applied by muscle and ligament tension. The swelling pressure (Ps) of the nucleus is directly dependent on the concentration and fixed charge densities of proteoglycan, i.e., the higher the concentration and fixed charge densities of proteoglycan the higher will be the swelling pressure of the nucleus. The external pressure changes with posture. When the human body is supine the compressive load on the third lumbar disc is 300 newtons (N) which rises to 700 N when an upright stance is assumed. The compressive load increases, yet again, to 1200 N when the body is bent forward by only 20°. Of course, the load is even higher under various physical activities.

When the external pressure (Pa) increases the previous balance, i.e., Ps=Pa, is upset. To reach a new balance the swelling pressure has to increase. This increase is achieved by increasing the proteoglycan concentration in the nucleus which is achieved by reducing the fluid in the nucleus. That is why discs lose about 10% of their height, as a result of creep, during the daytime. When the external load is released i.e., Ps is greater than Pa, the nucleus will imbibe fluid from its surroundings in order to reach the new equilibrium value. It is this property of the nucleus that is mainly responsible for the compressive properties of the disc.

The annulus forms the outer limiting boundary of the disc. It is composed of highly structured collagen fibers embedded in an amorphous base substance which is also composed of water and proteoglycans. The amount of proteoglycans is lower in the annulus than in the nucleus. The collagen fibers of the annulus are arranged in concentric laminated bands or lamella, (about 8-12 layers thick) with a thicker anterior wall and thinner posterior wall. In each lamella, the fibers are parallel and attached to the superior and inferior vertebral bodies at an angle of about 30° from the horizontal plane of the disc in both directions. This design particularly resists twisting because the half of the fibers cocked in one direction will tighten as the vertebrae rotate relative to each other in the other direction. The composition of the annulus along the radial axis is not uniform. There is a steady increase in the proportion of the collagen from the inner to the outer sections of the annulus. This difference in composition may reflect the need of the inner and outer regions of the annulus to blend into very different tissues while maintaining the strength of the structure. Only the inner lamellae are anchored to the end-plates forming an enclosed vessel for the nucleus. The collagen network of the annulus restrains the tendency of the nucleus gel to absorb water from surrounding tissues and swell. Thus, the collagen fibers in the annulus are always in tension, and the nucleus gel is always in compression.

The two vertebral end-plates are composed of hyaline cartilage, which is a clear, "glassy" tissue, that separates the disc from the adjacent vertebral bodies. This layer acts as a transitional horizontal zone between the hard, bony vertebral bodies and the soft disc. Because the intervertebral disc is avascular, most nutrients that the disc needs for metabolism are transported to the disc by diffusion through the end plate area.

The intervertebral joint exhibits both elastic and viscous behavior. Hence, during the application of a load to the disc there will be an immediate "distortion" or "deformation" of the disc, often referred to as "instantaneous deformation." It has been reported that the major pathway by which water is lost, from the disc during compression, is through the cartilage end-plates. Since the water permeability of the end-plates is in the range of about 0.20 to about $0.85 \times 10^{-17}$ $m^4 N^{-1} sec^{-1}$ it is reasonable to assume that under loading, the initial volume of the disc is constant while the load is applied. Because the natural nucleus of the disc is in the form of a loose hydrogel, i.e., a hydrophilic polymeric material which is insoluble in water, it can be deformed easily, the extent of deformation of the disc being largely dependent on the extensibility of the annulus. It is generally believed that the hydrostatic behavior of the nucleus plays an important role in the normal static and dynamic load-sharing capability of the disc and the restoring force of the stretched fibers of the annulus balances the effects of the nucleus swelling pressure. Without the constraint by the annulus, annular bulging of the nucleus would increase considerably. If the load is maintained at a constant level, a gradual change in joint height, commonly referred to as "creep", will occur as a function of time. Eventually, the creep will stabilize and the joint is said to be in "equilibrium." When the load is removed the joint will gradually "recover" to its original height before loading. The creep and relaxation rates depend on the amount of load applied, the permeability of the end-plates and the water binding capability of the nucleus hydrogel. Creep and relaxation are essential processes in pumping fluid in and out of the disc.

Degeneration of the intervertebral disc is believed to be a common cause of final pathological changes and back pain. As the intervertebral disc ages it undergoes degeneration. The changes that occur are such that, in many respects, the composition of the nucleus seems to approach that of the inner annulus. Intervertebral disc degeneration is, at least in part the consequence of compositional changes in the nucleus. It has been found that both the molecular weight and the amount of proteoglycans in the nucleus decrease with age, especially in degenerated discs, and the ratio of keratin sulphate to chondroitin sulphate in the nucleus to chondroitin sulphate and decrease in proteoglycan content decreases the fixed charged density of the nucleus from about 0.28 meq/ml to about 0.18-0.20 meq/ml. These changes cause the nucleus to lose part of its water binding capability which decreases the maximum swelling pressure it can exert. As a result, the maximum water content drops from over about 85%, in preadolescence, to about 70-75% in middle age. The glycosaminoglycan content of prolapsed discs has been found to be lower, and the collagen content higher, than that of normal discs of a comparable age. Discs L-4-L-5 and L-5-S-1 are usually the most degenerated *discs*.

It is known that although the nucleus only occupies about one third of the total disc area, it takes about 70% of the total loading in a normal disc. Thus, it has been found that the compressive load on the nuclei of moderately degenerated discs is about 30% lower than in comparable normal discs but the compressive load on the annulus increases by 100% in the degenerated discs. This load change is primarily caused by the structural changes in the disc as discussed above. The excess load on the annulus, of the degenerated disc, causes reduction of the disc height and excessive movement of the spinal segments. The flexibility of the disc produces excessive movement of the collagenous fibers which, in turn, injures the fiber attachments and causes delamination of the well-organized fibers of the annulus ring. The delaminated annulus can be further weakened by stress on the annulus and in severe cases this stress will cause tearing of the annulus. This whole process is very similar to driving on a flat tire, where the reinforcement layer will eventually delaminate. Because the thickness of the annulus is not uniform, with the posterior portions being thinner than the anterior portions, delamination and lesions usually occur in the posterior area first.

The spinal disc may also be displaced or damaged due to trauma or diseases. In these cases, and in the case of disc degeneration, the nucleus may herniate and/or protrude into the vertebral canal or intervertebral foramen, in which case it is known as a herniated disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve.

There are basically three types of treatment currently being used for treating low back pain caused by injured or degenerated discs: conservative care, discectomy and fusion. Each of these treatments has its advantages and limitations. The vast majority of patients with low back pain, especially those with first time episodes of low back pain, will get better with conservative care treatment. However, it is not necessarily true that conservative care is the most efficient and economical way to solve the low back pain problem.

Discectomy usually provides excellent short term results in relieving the clinical symptoms, by removing the herniated disc material, usually the nucleus, which causes the low back pain either by compressing the spinal nerve or by chemical irritation. Clearly, a discectomy is not desirable from a biochemical point of view. In a healthy disc, the nucleus takes the most compressional load and in a degenerated disc this load is primarily distributed onto the annulus ring which, as described above, causes tearing and delamination of the annulus. Removal of the nucleus in a discectomy actually causes distribution the compressive load onto the annulus ring thereby narrowing the disc spaces. It has been reported that a long-term disc height decrease might be expected to cause irreversible osteoarthritis-like changes in the facet joint. That is why discectomy yields poor long-term benefits and results in a high incidence of reherniation.

Fusion generally does a good job eliminating symptoms and stabilizing the joint. However, because the motion of the fused segment is restricted, the range of motion of the adjoining vertebral discs is increased possibly enhancing their degenerative processes.

Because of these disadvantages, it is desirable to use a prosthetic joint device that not only is able to replace the injured or degenerated intervertebral disc, but also can mimic the physiological and the biochemical function of the replaced disc. Such a device would restore the normal functions of the disc and prevent further degeneration of the surrounding tissue.

Artificial discs are well known in the prior art. U.S. Pat. No. 3,867,728, to Substad et al., relates to a device which replaces the entire disc. This device is made by laminating vertical, horizontal or axial sheets of elastic polymer. U.S. Pat. No. 3,875,595 to Froning relates to a collapsible plastic bladder-like prosthesis of nucleus pulposus. U.S. Pat. No. 4,309,777, to Patil, relates to a prosthesis utilizing metal springs and cups. A spinal implant comprising a rigid solid body having a porous coating on part of its surface is shown in Kenna's U.S. Pat. No. 4,714,469. An intervertebral disc prosthesis consisting of a pair of rigid plugs to replace the degenerated disc is referred by Kuntz, U.S. Pat. No. 4,349,921. U.S. Pat. Nos. 4,772,287 and 4,904,260 to Ray et al., relate to the use of a pair of cylindrical prosthetic intervertebral disc capsules with or without therapeutical agents. U.S. Pat. No. 4,911,718, to Lee et al., relates to an elastomeric disc spacer comprising three different parts; nucleus, annulus and end-plates, of different materials. At the present time, none of these inventions has become a product in the spinal care market. Bao et al., in U.S. Pat. Nos. 5,047,055 and 5,192,326 (assigned to the assignee of this invention and incorporated herein by reference) describe artificial nuclei comprising hydrogels in the form of large pieces shaped to conform to the shape of the disc cavity or beads within a porous envelope, respectively. The hydrogels have an equilibrium water content (EWC) of at least about 30% and a compressive strength of at least about 1 meganewtons per square meter (1 $MNm^{-2}$) when subjected to the constraints of the annulus and end plates of the disc. Preferably, the compressive strength of the nucleus is about 4 $MNm^{-2}$ when measured as described in U.S. Pat. Nos. 5,047,055 and 5,192,326.

A hydrogel is a network of a hydrophilic polymer(s) in which a large amount of water is present. In general, the water content is at least 20% by weight. In order to keep the hydrogel from being dissolved by the water, the polymer network must be crosslinked either physically or chemically. The water content (and therefore physical size) of hydrogels with either or both types of crosslinks may be sensitive to a variety of environmental conditions depending on the polymer. These environmental conditions include pH, temperature, electric field, and ionic strength & type.

Physically crosslinked hydrogels are semi-crystalline forms of the polymeric material. The crystalline domains are locations where the polymer chains are neatly packed. The crystalline domains are suspended in the amorphous (i.e., loosely packed, unordered) regions of the polymer, and in order for the crystalline domains to grow they must pull polymer chains from the amorphous regions. As the material becomes more crystalline the equilibrium water content is reduced. The material will continue to become more crystalline until the mobility of the polymer chains in the amorphous regions of the polymer is reduced to the point that they cannot be drawn into the crystalline structure. At this point the polymeric material has reached its equilibrium crystallinity. When using a hydrogel material in an implant, it can be advantageous to ensure that the polymeric material has reached its equilibrium crystallinity prior to being placed in vivo so that the material properties and size are stable.

Certain types of ions can help to increase the rate at which polymer chains in the amorphous regions of the material are drawn into the crystalline regions. The ions that have the greatest effect will depend on the type of polymer. In addition, a greater concentration of ions may increase the rate of crystalline growth. In the case of PVA, potassium has a greater effect than sodium on the rate of crystallinity (as measured by mass change) when comparing cations. The carbonate ion has a greater effect than chloride when comparing anions. Therefore, potassium carbonate should have a greater effect than sodium chloride on the rate at which a PVA hydrogel will reach its equilibrium crystallinity.

Due to the high water content of hydrogels, there has been interest in using these materials in a variety of medical devices. These devices include those intended for both short (such as a cervical dilator) & long term (such as a non-throbogenic coating for vascular grafts) exposure to the body, and also both load bearing (such as an artificial articular cartilage) and non-load bearing devices (such as contact lenses).

The primary disadvantage of the inventions of Stubstad et al., Patil, Kenna and Lee et al. is that use of their prostheses requires complete replacement of the natural disc which involves numerous surgical difficulties. Secondly, the intervertebral disc is a complex joint, anatomically and functionally, comprising the aforementioned three component structures, each of which has its own unique structural characteristics. Designing and fabricating such a complicated prosthesis from acceptable materials, which will mimic the function of the natural disc, is very difficult. A further problem is the difficulty of preventing the prosthesis from dislodging. Fourthly, even for prostheses which are only intended for replacing the nucleus, a major obstacle has been to find a material which is similar to the natural nucleus and is also able to restore the normal function of the nucleus.

Hydrophobic elastomers and thermoplastic polymers are not desirable for use in the prosthetic nuclei due to their significant inherent differences from the natural nucleus e.g., lack of hydrophilicity, in the elastomers, and lack of flexibility in the thermoplasts.

These problems are not solved by Kuntz, who uses elastic rubber plugs, or by Froning and Ray et al., who use bladders or capsules, respectively, which are filled with a fluid or thixotropic gel. According to the Ray and Froning patents, liquid was used to fill the capsules and bladders, respectively, thereby requiring that their membranes be completely sealed to prevent fluid leakage. As a consequence, those devices cannot completely restore the function of the nucleus which allows body fluid to diffuse in and out during cyclic loading thereby providing the nutrients the disc needs.

The Bao et al. prosthetic lumbar disc nuclei are made from hydrogels. Hydrogels have been used in biomedical applications, such as contact lenses. Among the advantages of hydrogels is that they are more biocompatible than hydrophobic elastomers and metals. This biocompatibility is largely due to the unique characteristics of hydrogels in that they are soft and contain water like the surround tissues and have relatively low frictional coefficients with respect to the surrounding tissues. The biocompatibility of hydrogels results in prosthetic nuclei which are more easily tolerated in the body. Furthermore, hydrophobic elastomeric and metallic gels will not permit diffusion of aqueous compositions, and their solutes, therethrough.

An additional advantage of some hydrogels is their good mechanical strength which permits them to withstand the load on the disc and restore the normal space between the vertebral bodies. The aforementioned nuclei of Bao et al. have high mechanical strength and are able to withstand the body loads and assist in the healing of the defective annuli.

Other advantages of the hydrogels, used in the Bao et al. nuclei, are their excellent viscoeleastic properties and shape memory. Hydrogels contain a large amount of water which acts as a plasticizer. Part of the water is available as free water which has more freedom to leave the hydrogel when the hydrogel is partially dehydrated under mechanical pressure. This characteristic of the hydrogels enables them to creep, in the same way as the natural nucleus, under compression, and to withstand cyclic loading for long periods without any significant degradation or loss of their elasticity. This is because water in the hydrogel behaves like a cushion whereby the polymeric network of a hydrogel with a high EWC is less susceptible to damage under mechanical load.

Another advantage of hydrogels is their permeability to water and water-soluble substances, such as nutrients, metabolites and the like. It is known that body fluid diffusion, under cyclic loading, is the major source of nutrients to the natural disc. If the route of this nutrient diffusion is blocked, e.g., by a water-impermeable nucleus, further deterioration of the disc will ensue.

Hydrogels can be dehydrated and hydrated again. When a hydrogel is dehydrated, its volume decreases, thereby facilitating implantation of the prosthetic nucleus into the nuclear cavity in the disc. The implanted prosthetic nucleus will then swell, in the body, by absorption of body fluid up to its EWC. Alternately, the device may be inserted into the disc at its approximate in vivo equilibrium water content for the expected lumber intradiscal pressure for the patient. The equilibrium water content will vary depending on the position of the patient during implantation. The patient is positioned differently depending on whether the anterior, lateral or posterior approach is used by the surgeon for implanting the hydrogel nucleus.

The EWC of the hydrogel is adjusted to match the anticipated pressure on the implant at implantation so the EWC does not change after implantation. The EWC of a hydrogel depends on the compressive load applied thereto. Thus, the EWC of a specific hydrogel in an open container will differ from the EWC of the same hydrogel in a closed vessel such as an intervertebral disc. The EWC values, referred to below, are for hydrogels subjected to compressive loads under the conditions found in an intervertebral disc. The expansion factor of a dehydrated hydrogel, in turn, is dependent on its EWC. Thus, it may vary from 1.19 for a hydrogel of 38% EWC to 1.73 for a hydrogel of 80% EWC. For an 80% EWC hydrogel, the volume of the dehydrated prosthetic nucleus is usually about 20% of that of the hydrated one. The ability to be dehydrated and then return to its original shape upon hydration, up to its EWC, makes it possible to implant the device posterior-laterally, during surgery, thereby reducing the complexity and risk of intraspinal surgery as traditionally used. The danger of perforation of the nerve, dural sac, arteries and other organs is also reduced. In addition, the incision area on the annulus can be reduced, thereby helping to heal the annulus and prevent the reherniation of the disc. Hydrogels are also useful for drug delivery into the disc due to their capability for controlled release of drugs. Various therapeutic agents, such as growth factors, long term analgesics, antibiotics and anti-inflammatory agents can attach to the prosthetic nucleus and be released in a controllable rate after implantation of the nucleus in the disc.

Furthermore, dimensional integrity can be maintained with hydrogels having a water content of up to about 90%. This dimensional integrity, if the nucleus is properly designed, will aid in distributing the vertebral load to a larger area on the annulus ring and prevent the prosthetic nucleus from bulging and herniating.

SUMMARY OF THE INVENTION

It is an object of this invention to provide a method for forming a high strength hydrogel implant which exhibits a constant swelling pressure profile (water content change with respect to applied pressure) immediately upon implantation in a dehydrated state. It is a further object of the invention to provide an artificial nuclear implant which has stable swelling pressure characteristics immediately after implantation and onward. It is yet another object of the invention to provide a method for providing an artificial nuclear implant which maintains a uniform disc spacing based on disc loading after implantation at all times after implantation.

These and other objects are achieved by a method for forming a high strength hydrogel medical implant which includes preparing a hydrogel solution, injecting the solution into a mold and causing the molded solution to gel. The molded gel is then washed in a physiologic solution such as a saline solution for between two to twelve weeks. The saline solution may contain between 0.025 M and 0.25 M and preferably between 0.025 M and 0.05 M solution of potassium carbonate ($K_2CO_3$). Besides a solution containing potassium carbonate any physiologic solution having an ionic charge could be used, for example, serum at a Ph that would allow some or all proteins to be charged. After the hydrogel solution has been washed from between two to twelve weeks, it is dehydrated and packaged. By dehydration, it is meant that the water content of the hydrogel is reduced to about 55%. The saline solution used is preferably a 0.9% phosphate buffered sodium chloride solution to which the potassium carbonate is added at a concentration of between 0.025M and 0.25M.

The washing process may run from one (1) day to twelve (12) weeks and preferably from two (2) to twelve (12) weeks and most preferably for twelve (12) weeks.

The saline solution is changed regularly, for example, two, three, five or more times a week during the washing process. In addition, the concentration of the potassium carbonate solution can be changed during the washing period with a more concentrated 0.05 M solution being used during the first 2 to 4 weeks and then a lower concentration solution of about 0.025 M potassium carbonate being used for the last 4 to 8 weeks of washing. Normally, the hydrogel is irradiated after washing in a hydrated state of about 75% water content.

It has been found that washing the hydrogel implants after gelation in a physiologic saline rather that water ensures that the swelling pressure characteristics of the material used in the artificial nucleus implant would remain stable after implantation. Results showing that washing the implants in saline creates a hydrogel material that does not undergo swelling pressure property changes in vivo.

One of the most important properties of any load-bearing hydrogel implant is the swelling pressure characteristic (i.e. water content vs. externally applied pressure) of the material used in the implant. Early results from a pre-clinical safety studies have shown that the swelling pressure characteristics of the water-washed PVA hydrogel was not constant during the first 4 weeks in vivo, with no further changes occurring at later time points. These changes indicate that the implant may have a lower in vivo equilibrium water content immediately after implantation than originally estimated, and would therefore have a smaller volume. This reduction in implant volume would have no bearing on the safety of the device, but could have an effect on the ability of the implant to maintain disc height. Maintenance of disc height is a parameter that may be assessed in a clinical study to evaluate efficacy of the implant.

DETAILED DESCRIPTION OF THE PREFERRED EMBODIMENTS

One of the most important properties of any load-bearing hydrogel implant is the swelling pressure characteristic of the material used in the implant. The swelling pressure characteristic of a hydrogel describes the relationship between applied load and equilibrium water content. In general, a larger load on the material will result in a reduced water content. This phenomenon has been well documented for the nucleus pulposus of the intervertebral disc, which is a hydrogel.

It is important for any load-bearing implant made from a hydrogel material to have a stable swelling pressure characteristic after implantation. If the swelling pressure characteristic of the implant changes over time it may be difficult to predict the equilibrium water content and size of the implant. Early results from a pre-clinical safety study evaluating an artificial nucleus pulposus implant made from a water-washed poly (vinyl alcohol) (PVA) hydrogel showed that the swelling pressure characteristic had changes compared to an unimplanted control after 4 weeks in vivo, with no further changes occurring at later time points.

Figure 1:
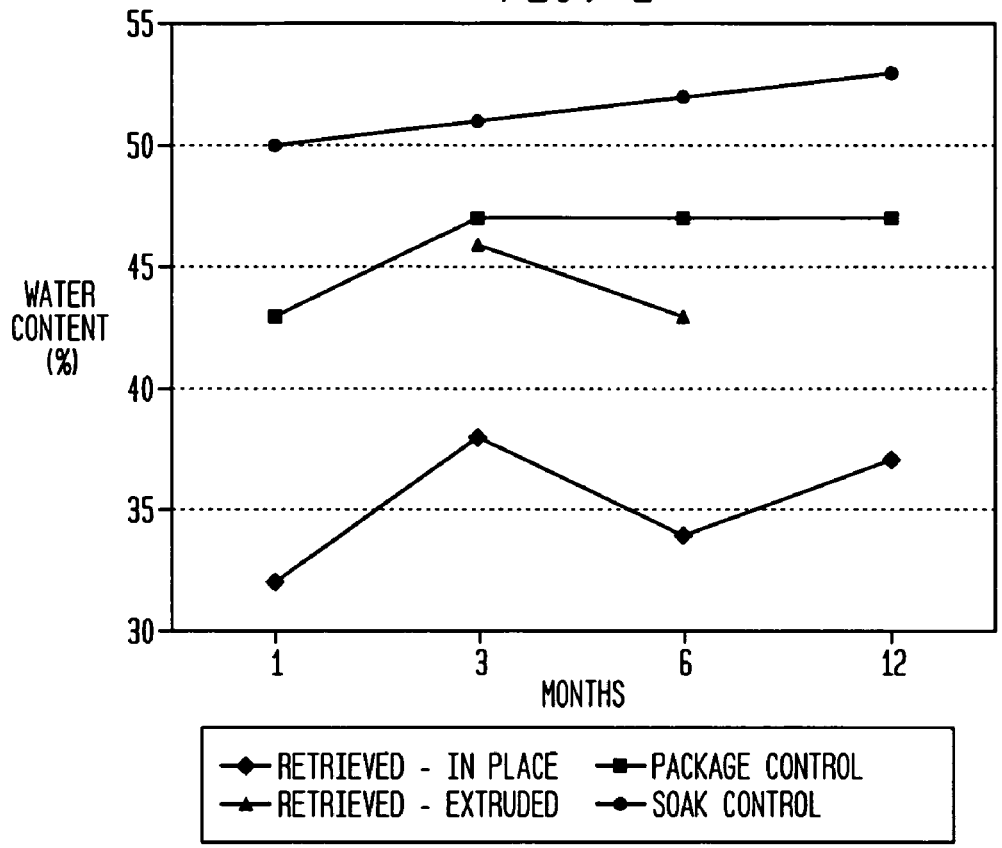
FIG. 1 shows that water-washed implants that have been implanted into the disc space will have a lower water content than control implants when subjected to 1.1 MPa of osmotic pressure. The figure shows that less than one month of exposure to the physiologic environment is responsible for this result and no further changes occur at later time points.
Figure 2:
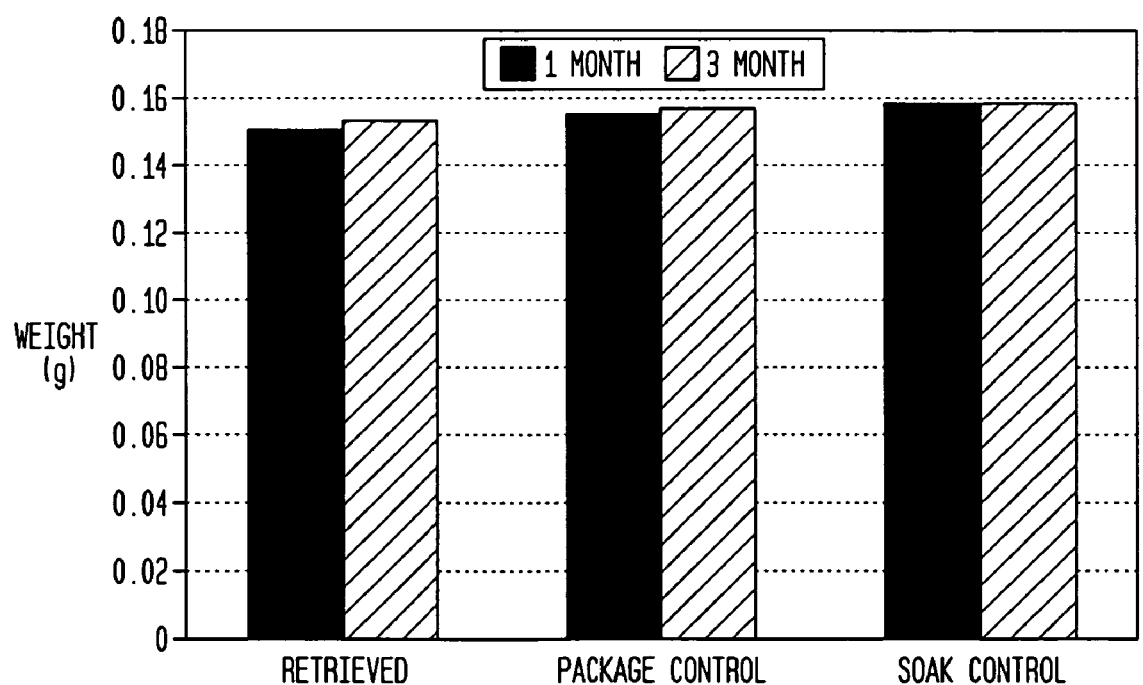
FIG. 2 shows that saline-washed implants (which have been pre-exposed to a physiologic environment prior to implantation) that have been implanted into the disc space will have a similar water content to control implants when subject to 1.1 MPa of osmotic pressure.

Washing the implants after gelation in a physiologic saline solution rather that water was adopted in order to ensure that the swelling pressure characteristics of the material used in the artificial nucleus implant would remain stable after implantation. This change to the method used to process the material was successful as shown in FIGS. 1 and 2. The results of washing the implants in saline on the swelling pressure characteristic can be seen at the one-month time point, and are merely confirmed by results from later time points.

EXAMPLE 1

Figure 3:
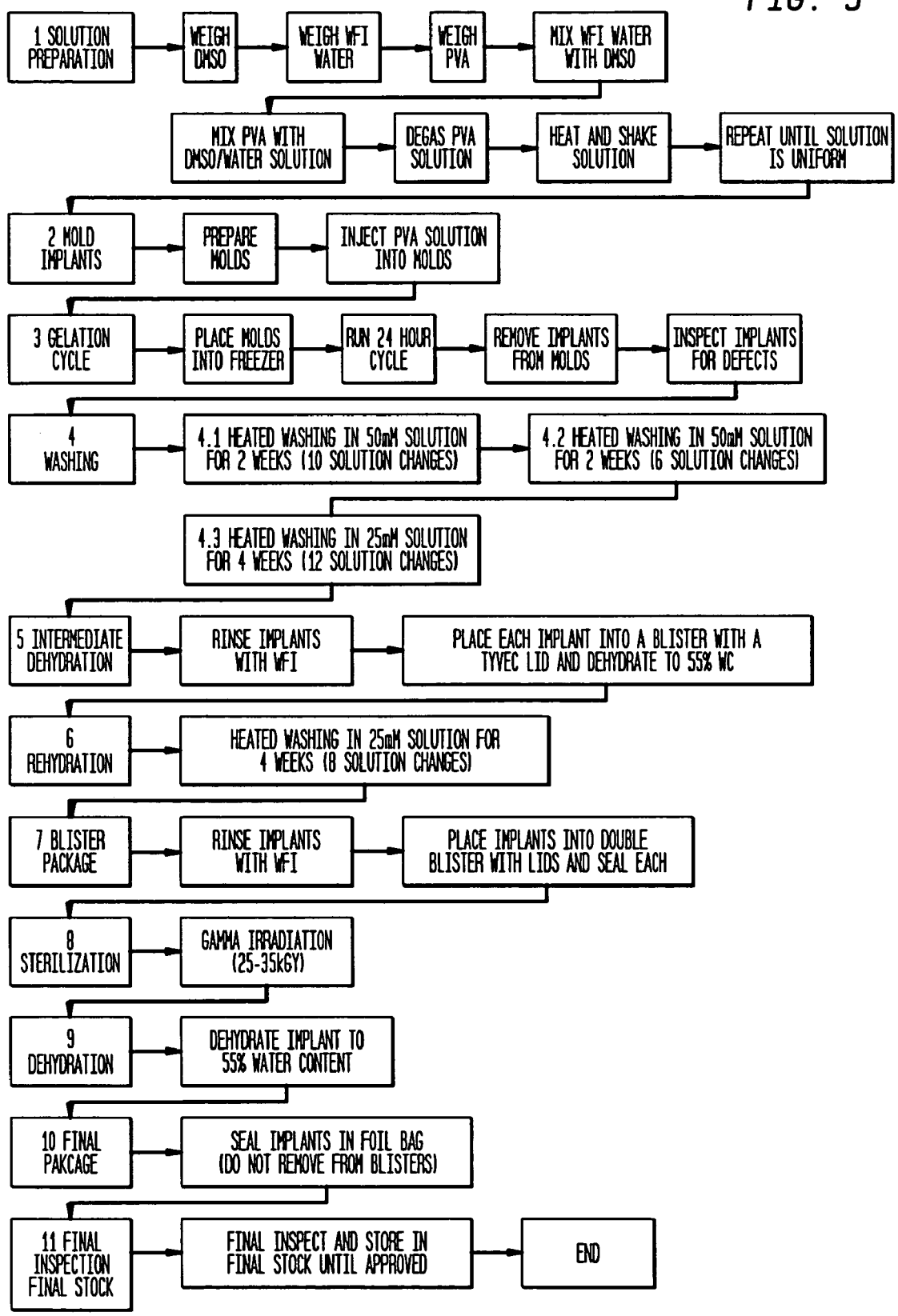
FIG. 3 is a process flow chart for forming the spinal nucleus of the present invention.

The implants used in this study were fabricated in a class 1,000 clean room using the manufacturing flow chart of FIG. 3. The implants were made from a 98.5% hydrolyzed (PVA-117, Kuraray, Japan) poly (vinyl alcohol) (PVA) hydrogel that is physically crosslinked through the use of a freezing-thawing technique. Any water used in the fabrication of the device was USP Sterile Water-for-Injection (WFI) (Abbott Laboratories, North Chicago, Ill.). All of the implants tested were washed for twelve weeks in 0.9% phosphate buffered saline (PBS) (cat. #1000-3, Sigma Diagnostics, St. Louis, Mo.) with 50 mM potassium carbonate (SigmaUltra, cat. #P-5833, Sigma Chemical Co., St. Louis, Mo.) for the first 4 weeks of the wash cycle. The implants were then washed in PBS plus 25 mM potassium carbonate for the last 8 weeks of the wash cycle. The implants were sterilized with 25-35 kGy of gamma sterilization and implanted at their approximate in vivo equilibrium water content which was at approximately 55% water content.

The PVA hydrogel material submitted for irradiation had approximately 80% water content. Due to irradiation induced crosslinking the material had about 78% water content after sterilization. After subsequently being dehydrated to 55% water content the maximum hydration level upon rehydration is about 75% water content. A comparison of the ionic concentration of the 25 mM $K_2CO_3$ wash solution (assuming full dissociation) and human plasma is shown in Table I.

The PBS and potassium carbonate washing solutions were heated to 37° C. and the solutions were changed five times a week for the first two weeks and two or three times a week thereafter. The solution changes were required to reduce bioburden.

TABLE I

Ionic Concentration (mM) of the Final Saline Wash Solution and Human Plasma

| | $Na^+$ | $K^+$ | $Ca^{+2}$ | $Mg^{+2}$ | $Cl^-$ | $HCO_3^-$ $CO_3^{-2}$ | $H_2PO_4^-$ $HPO_4^{-2}$ | $SO_4^{-2}$ |
|---|---|---|---|---|---|---|---|---|
| Human Plasma | 142 | 5 | 2.5 | 1.5 | 103 | 27 | 1 | 0.5 |
| Wash Solution | 137 | 54.2 | 0 | 0 | 122.7 | 25 | 10 | 0 |

Figure 4:
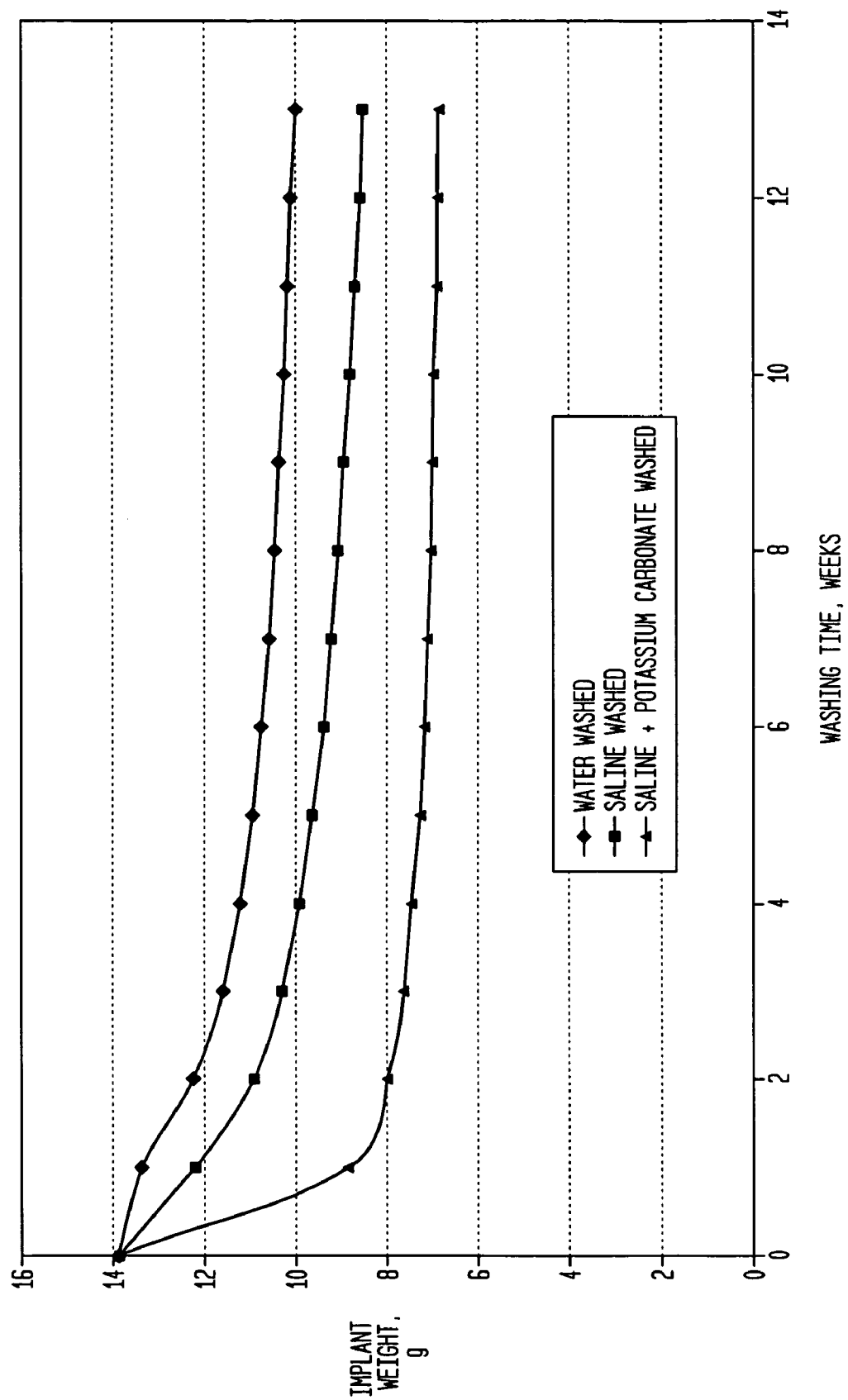
FIG. 4 is a chart showing the weight change versus time with three different wash solutions.

A test designed to show the effects of different wash solutions on a PVA hydrogel was performed. In this test three different wash solutions were evaluated: [1] USP water for injection (WFI); [2] 0.9% phosphate buffered sodium chloride in WFI (saline), and [3] the saline plus 25 mM potassium carbonate. The effect of the wash solution was determined by weighing the test samples. As the hydrogel becomes more crystalline, the polymer chains become more tightly packed, and the material can hold less water and will therefore have less mass (other tests have been performed which shows that the mass loss is not due to polymer washing out of the material). The results from first 13 weeks of this test are shown in FIG. 4.

By properly selecting the wash solution to which the hydrogel material is exposed, the processing time required for it to reach equilibrium could be reduced. In addition, an intermediate dehydration step (such as halfway through the wash cycle) may be performed to enhance cross-link formation and reduce overall wash time.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for forming a high strength hydrogel medical implant comprising:
   preparing a polymer solution;
   injecting the solution into a mold;
   causing said molded solution to gel by physically cross-linking the solution;
   adjusting the equilibrium hydrogel crystallinity to insure that the swelling pressure of the hydrogel remains stable after implantation by washing said molded gel in a physiologic solution;
   dehydrating the molded gel; and
   packaging the implant.

2. The method as set forth in claim 1 wherein said washing takes place for about one day to twelve weeks.

3. The method as set forth in claim 2 wherein the washing takes place from two weeks to twelve weeks.

4. The method as set forth in claim 2 wherein the solution contains 0.9% by weight phosphate buffered sodium chloride solution.

5. The method as set forth in claim 4 wherein the sodium chloride solution further is mixed with a potassium carbonate solution.

6. The method as set forth in claim 5 wherein the potassium carbonate solution is between about 0.025 M and 0.05 M.

7. The method as set forth in claim 6 wherein a 0.05 M potassium carbonate solution is used for a first portion of the washing and a 0.025 M potassium carbonate solution is used for a later portion of the washing.

8. The method as set forth in claim 1 wherein the dehydration reduces the water content of the gel to its approximate in vivo equilibrium water content.

9. The method as set forth in claim 8 further including irradiating the molded gel after said washing with gamma irradiation.

10. The method as set forth in claim 9 wherein said molded gel is hydrated to about 80% water content prior to irradiation.

11. The method as set forth in claim 4 wherein said washing in said 0.9% by weight phosphate buffered sodium chloride solution is for at least two weeks.

12. The method as set forth in claim 11 wherein said buffered sodium chloride solution includes potassium phosphate.

13. A process for treating a hydrogel comprising:
forming a hydrogel from a polymer solution by physically cross-linking the polymer; and
adjusting the equilibrium hydrogel crystallinity to insure that the swelling pressure of the hydrogel remains stable after implantation by washing the hydrogel in a physiologic solution.

14. The process for treating a hydrogel as set forth in claim 13, wherein the physicologic solution contains between 0.025 and 0.05 M potassium carbonate.

15. The process for treating a hydrogel as set forth in claim 14, wherein the washing takes place for at least one day.

16. The process for treating a hydrogel as set forth in claim 15, wherein the washing takes place for between one day and 12 weeks.

17. The process for treating a hydrogel as set forth in claim 13, wherein the washing solution is heated.

18. The process for treating a hydrogel as set forth in claim 17 wherein the solution is heated to 37° C.

19. The process for treating a hydrogel as set forth in claim 13, wherein the solution is a 0.9% by weight phosphate buffered sodium chloride solution with between 0.025 M and 0.25 M potassium carbonate added thereto.

20. The process as set forth in claim 19 wherein the potassium carbonate added is between 0.025 M and 0.05 M.

21. The method as set forth in claim 1 wherein the gel formed is semi-crystalline.

22. The method as set forth in claim 21 wherein the washing is done for two to twelve weeks in a 0.9% by weight phosphate buffered sodium chloride solution.

23. The method as set forth in claim 22 wherein the solution further contains potassium carbonate.

24. The method as set forth in claim 21 wherein the physiologic solution has an ionic charge.

25. The method as set forth in claim 1 wherein the polymer is poly (vinyl alcohol).

26. The method as set forth in claim 1 wherein the hydrogel is physically cross-linked by a freezing-thawing technique.

27. A method of forming a hydrogel medical implant comprising:
preparing a polymer solution;
physically cross-linking the solution to form a semi-crystalline gel using a freezing-thawing technique;
adjusting the equilibrium hydrogel crystallinity to insure that the swelling pressure of the hydrogel remains stable after implantation by washing the gel in a saline solution which further contains physiologic carbonate for at least one day.

28. The process for treating a hydrogel as set forth in claim 27 wherein the solution is a 0.9% by weight phosphate buffered sodium chloride solution with between 0.025 M and 0.25 M potassium carbonate added thereto.

29. The method as set forth in claim 27 further including irradiating the molded gel after said washing with gamma irradiation.

30. The method as set forth in claim 27 wherein the polymer is poly (vinyl alcohol).

* * * * *